US007257953B2

(12) United States Patent
Rada

(10) Patent No.: US 7,257,953 B2
(45) Date of Patent: Aug. 21, 2007

(54) APPARATUS AND METHOD FOR PREPARING FROZEN TISSUE SPECIMENS

(76) Inventor: David C. Rada, 248 Lake Shore West, Lake Quivira, KS (US) 66106

( * ) Notice: Subject to any disclaimer, the term of this patent is extended or adjusted under 35 U.S.C. 154(b) by 322 days.

(21) Appl. No.: 11/111,431

(22) Filed: Apr. 21, 2005

(65) Prior Publication Data

US 2006/0236703 A1    Oct. 26, 2006

(51) Int. Cl.
F25B 19/00 (2006.01)
F25D 25/02 (2006.01)

(52) U.S. Cl. .......................... 62/51.1; 62/381

(58) Field of Classification Search .............. 62/51.1, 62/341, 381, 378, 383, 499
See application file for complete search history.

(56) References Cited

U.S. PATENT DOCUMENTS

| | | | | | |
|---|---|---|---|---|---|
| 3,209,821 | A | * | 10/1965 | Zeytoonian | 165/185 |
| 3,218,896 | A | * | 11/1965 | McCormick | 83/15 |
| 4,545,831 | A | * | 10/1985 | Ornstein | 156/57 |
| 4,695,339 | A | | 9/1987 | Rada | |
| 4,751,828 | A | * | 6/1988 | Coulter et al. | 62/51.1 |
| 4,752,347 | A | | 6/1988 | Rada | |
| 5,103,651 | A | * | 4/1992 | Coelho et al. | 62/341 |
| 5,321,955 | A | * | 6/1994 | Leonard | 62/51.1 |
| 5,628,197 | A | | 5/1997 | Rada | |
| 5,776,298 | A | * | 7/1998 | Franks | 156/390 |
| 5,817,032 | A | * | 10/1998 | Williamson et al. | 600/562 |
| 5,829,256 | A | | 11/1998 | Rada | |
| 6,094,923 | A | | 8/2000 | Rada | |
| 6,289,682 | B1 | | 9/2001 | Rada | |
| 6,536,219 | B2 | * | 3/2003 | Peters | 62/62 |
| 6,725,673 | B1 | | 4/2004 | Rada | |

FOREIGN PATENT DOCUMENTS

DE    4323483 A1 *    2/1994

OTHER PUBLICATIONS

*Histologic Margins in Conservative Lumpectomy*, a Proposal, Rada, David C., M.D., Publication Date: unknown, pp. 1-11.
*Intraoperative Histologic Assessment of Surgical Margins and Lymph Node Metastasis in Breast-Conserving Surgery*, Journal of Surgical Oncology 60:185-190, Publication Date: Jun. 29, 1995.

(Continued)

*Primary Examiner*—Mohammad M. Ali
(74) *Attorney, Agent, or Firm*—John C. McMahon

(57) ABSTRACT

An apparatus and method for preparing frozen tissue specimens includes a base supporting a pair of rotary motion platforms and a center platform. The rotary motion platforms are movable from an open, side-by-side position to a closed, center platform-covering position. The rotary motion platform includes a plurality of cryogenic discs, each identified for receiving a plurality of tissue samples. The center platform includes a plurality of cryogenic discs, each having a plurality of bores for receiving object holders thereon, each object holder for receiving a frozen specimen thereon. The center platform cryogenic discs each have a channel system with intersecting peripheral, chordal and radial channels. A moistening tray includes structure having a closed, object holder wetting position and an open, object holder elevating position. Further disclosed is the use of a tissue orientation map, usable on temporary tattoos and tissue receiving sheets for specimen orientation and mapping of tumor roots. Also disclosed are labels and identification methods, fiber-reinforced embedding compounds and the use of treated polyester sheets for tissue specimen placement.

19 Claims, 9 Drawing Sheets

OTHER PUBLICATIONS

*Intraductal Extension of Primary Invasive Breast Carcinoma Treated by Breast-Conservative Surgery*, Computer Graphic Three-Dimensional Reconstruction of the Mammary Duct-Lobular Systems, Ohtake, et al., Publication Date: Jan. 5, 1995, pp. 32 and 41.

*A New Method of Complete Peripheral Margin Assessment in Breast Conservative Surgery Using an Adjustable Polygonal Prism Mould*, Ichihara, et al., Department of Pathology, Nagoya National Hospital, Nagoya 460-0001, Publication Date: unknown, pp. 905-906.

*Determination of viscoelastic and rheo-optical material functions of water-soluble cellulose derivatives*, Clasen, et al., Prog. Polym. Sci. 26 (2001) 1839-1919, Publication Date: Jun. 20, 2001.

*Conformation and packing of various crystalline cellulose fibers*, Zugenmaier, Peter, Prog. Polym. Sci. 26 (2001) 1341-1417, Publication Date: Jun. 25, 2001.

*Characterization of water-soluble externally HCl-doped conducting polyaniline*, Takahaski, et al., Synthetic Metals 128 (2002) 27-33, Publication Date: Oct. 2, 2001.

*Short Communication Simple synthesis of water-soluble conducting polyaniline*, Ito, et al., Synthetic Metals 96 (1998) 161-163, Publication Date: May 8, 1998.

Brochure of Sakura, *Placing productivity in a new light*, pp. 1-8, Publication Date: 2004.

* cited by examiner

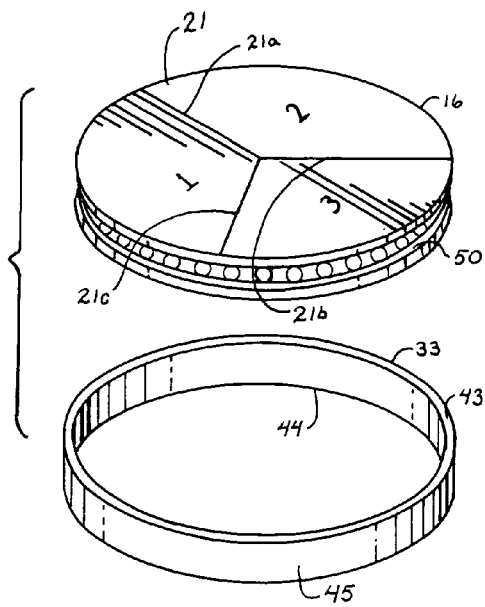
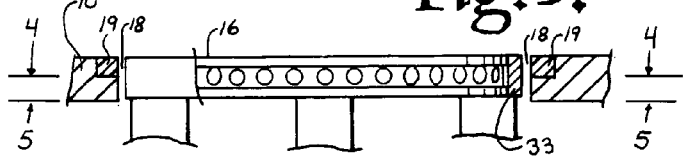
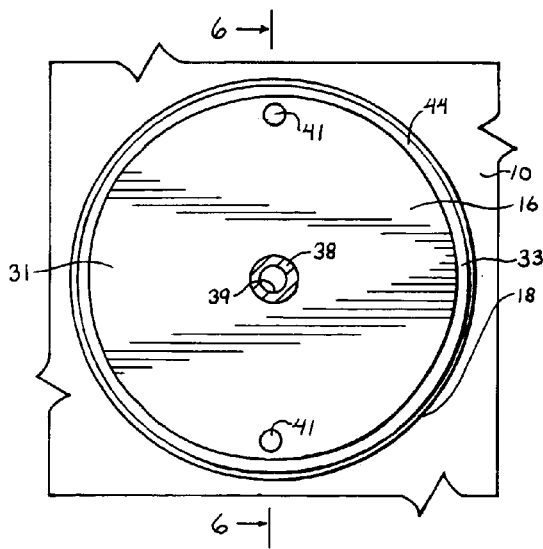
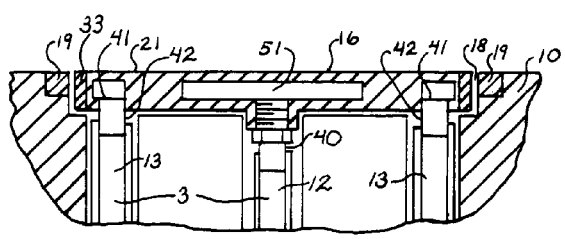

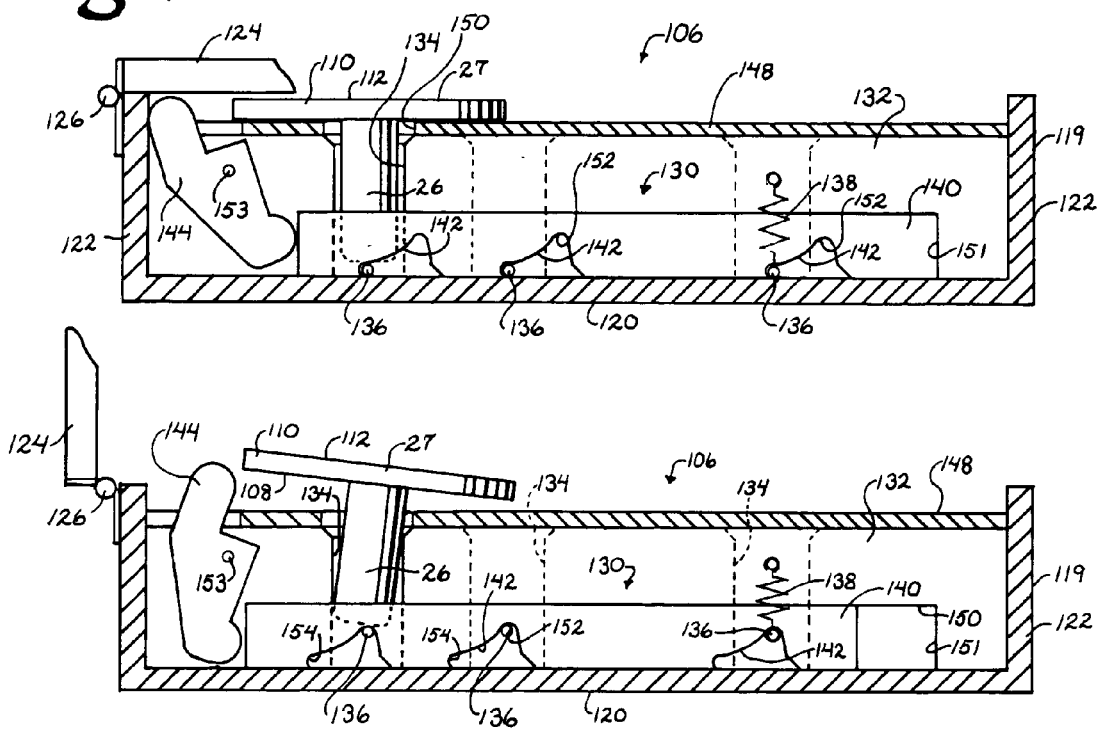
Fig. 13.
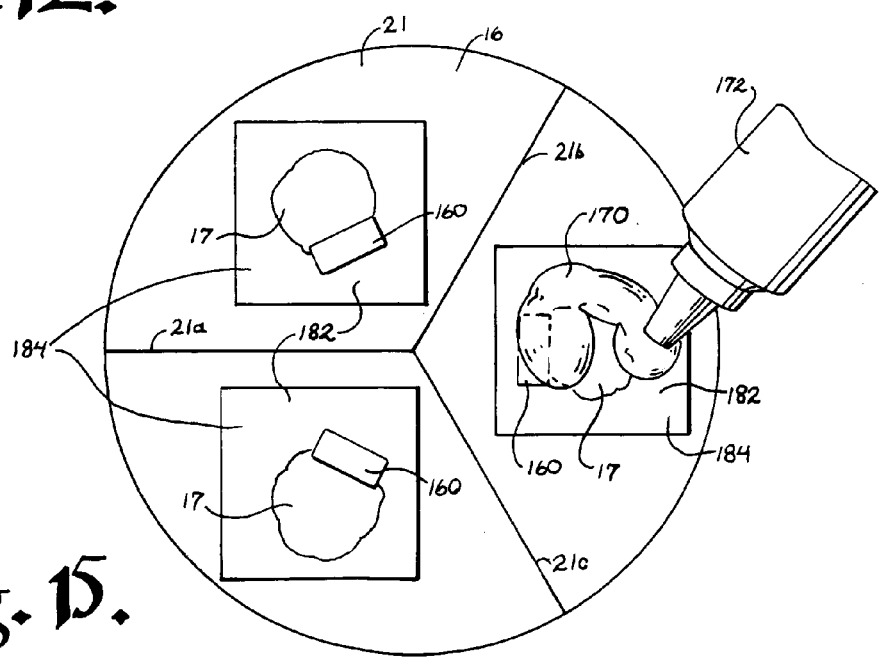
Fig. 12.
Fig. 15.

APPARATUS AND METHOD FOR PREPARING FROZEN TISSUE SPECIMENS

BACKGROUND OF THE INVENTION

The present invention is broadly directed to an improved apparatus and method for rapidly freezing a plurality of tissue specimens at cryogenic temperatures that enhances heat transfer, quickly cools tissue holders and tissue, facilitates cutting of thin tissue sections and facilitates tracking of tissue specimens throughout a tissue preparation and examination process. More particularly, the invention is directed to a multi-specimen tissue freezing apparatus and method of mapping and labeling, the apparatus including a channel system permitting highly effective circulation of a cryogen and transfer of heat thereto so as to rapidly cool tissue specimens.

Biopsy or surgical removal of tissue specimens for histologic examination is commonly employed for diagnostic purposes. When a lesion is known or suspected to be malignant, the entire mass is generally excised, if possible. An examination technique may be employed in which the entire tumor margin surface area is reviewed under a microscope. This technique involves microscopic screening of the exterior surface area of the tumor for the presence of malignant cells in order to ensure that all such cells have been removed. If practiced effectively, tumor margin surface area examination enhances the likelihood of complete removal of all cells of a localized malignancy.

Once harvested, the tissue sample is preferably quickly frozen at a controlled rate using a cryogenic coolant in order to obtain high quality frozen sections suitable for use in diagnosis. The tissue is then cut into thin layers or sections for histological examination. It is important that the tissue be frozen and the histologic examination performed as quickly as possible, since the patient must be kept waiting pending the microscopic evaluation, in case any additional tissue must be excised. In the past each review of the tissue was comparatively lengthy, so that a patient had to be maintained in a very uncomfortable state with an open wound for a long period of time. Much of the delay was due to slow freezing of the tissue samples, so fast freezing is very desirable, especially where multiple samples must be taken.

Controlled freezing of the tissue may be accomplished using the methods and devices set forth in Applicant's previous patents, such as U.S. Pat. Nos. 4,695,339; 4,752,347; 5,628,197; 5,829,256; 6,094,923, 6,289,682 and 6,725,673, which are incorporated herein by reference. The rate at which specimens can be frozen under such controlled conditions is determined by the rate of heat transfer from a cryogenic fluid, such as liquid nitrogen, to the platform on which the tissue is placed. Specimens must be frozen relatively quickly in order to avoid formation of large ice crystals. However, attempts to increase the rate of freezing by use of excessive amounts of cryogenic material may impair control over the freezing process. Specimens that are frozen unevenly or incorrectly may be marred by voids and artifacts that might impair histologic examination and diagnosis. It is also desirable to minimize the quantity of cryogenic fluid that is used, since such fluids are costly and may present certain environmental hazards which must be addressed. Therefore, it is important to enhance heat transfer while maintaining control over specimen freezing conditions and conserving use of cryogenic fluids.

Even a properly prepared tissue specimen that is quickly frozen under controlled conditions may not result in a high quality histologic specimen unless thin tissue sections can be taken easily from the frozen specimen. Compression of the section may occur where difficulty is encountered in cutting thin sections from a frozen specimen. Upon gross examination, compressed tissue sections may appear to be usable for mounting on slides, but will prove to be difficult to evaluate. Badly crumpled sections may be unusable.

Another problem faced in a busy laboratory is the proper identification of tissue samples as they travel from station to station, through the processes of tissue harvesting; preparations, such as relaxing and anatomic color marking before freezing; freezing which may include more than one step or transfer to and from freezing platforms; slicing; and examination. A further challenge is developing improved methods of mapping or marking both the patient and the tissue sample to ensure correct orientation of the tissue sample with respect to the patient if clinical reorientation is necessary for further tissue harvesting. Accordingly, there is a need for apparatus and methods for evenly and quickly freezing multiple tissue specimens under controlled conditions with correct labeling and mapping.

SUMMARY OF THE INVENTION

An apparatus according to the invention includes a base supporting at least one rotary motion platform and a center platform. The rotary motion platform or platforms are movable from an open, side-by-side position with respect to the center platform to a closed, center platform-covering position. Each platform includes a plurality of cryogenic discs, each identified with numerals printed or otherwise located thereon to aid in the placement and tracking of a plurality of tissue specimens during freezing and transfer of the specimens onto object holders.

Each rotary platform cryodisc is also equipped with a channel system for circulation of a cryogenic fluid within the disc structure that includes a peripheral channel and connecting radial channels. The center platform, that includes a plurality of bores for receiving object holders thereon, includes a channel system with a plurality of chordal and radial channels disposed between the bores, the chordal and radial channels communicating with a peripheral channel. Each of the cryodiscs includes a circumferential ring seal. The discs of the center platform include peripheral inlet and outlet ports.

According to an aspect of the invention, a moistening tray is provided for receiving the object holders and wetting undersides thereof with alcohol prior to placement of the object holders in the bores of the center cryodisc. The moistening tray includes a moistening pad and a holding structure. The holding structure has two positions: a first closed position wherein the object holders are received by the moistening tray with undersides thereof contacting the moistening pad; and a second open position wherein at least a portion of the object holders are in spaced relation with the moistening pad.

A method of quick freezing a tissue specimen by cooling the specimen on a rotary cryogenic disc and then transferring the specimen to an object holder includes the steps of placing up to a plurality of specimens on a single cryodisc to be cooled and then placing a unique label adjacent to each specimen on the cryodisc prior to cooling, each label having an identification sequence embedded throughout a thickness of the label, the label linking the particular specimen with a particular patient then traveling with the specimen throughout the freezing, transfer, slicing and examination steps of the process.

Another aspect of the invention includes the application of an embedding medium to each specimen prior to the transfer of the specimen to a corresponding object holder. Preferably, the embedding medium includes both fiber and an electrically conductive polymer. Additionally, the fiber-reinforced medium may include protein, such as a silk fiber. A preferred fiber for use in the embedding medium is bamboo cellulose. The electrically conductive polymer may be polyaniline or a long chain polyaniline emeraldine salt grafted to lignin.

In another alternative aspect of the invention, tissue specimens are placed on a sheet of surface treated polyester film rather than directly on the cryodisc to be cooled. Preferably, the surface of the polyester film is treated by brushing with albumin.

A further aspect of the invention is a tissue orienting pattern or grid for placement, for example on a patient in the form of a temporary tattoo that corresponds to markings on the tissue specimen. Such a grid or pattern may also be used on the tissue receiving polyester film previously described herein. The tissue orienting pattern aids in the location and ongoing tracking of tumor roots. A temporary tattoo having a tissue orienting pattern thereon may be applied to a patient prior to harvesting a tissue specimen therefrom with a portion of the tattoo remaining on the patient after tissue harvesting. A tissue orienting grid or pattern according to the invention preferably includes an X axis, a Y axis, and concentric circles, the X and Y axes including color coding cooperating with color coding on the tissue specimen.

OBJECTS AND ADVANTAGES OF THE INVENTION

Therefore, objects of the present invention include: providing an apparatus and method for rapidly freezing tissue samples; to provide such apparatus and methods wherein cryogenic fluid is used to rapidly cool discs associated with the receiving of opposite sides of a plurality of tissue samples; to provide such apparatus and methods that aid in the identification and tracking of a plurality of tissue samples; to provide such apparatus and methods to aid in the mapping of tissue samples if further tissue harvesting is deemed necessary; and to provide such apparatus and methods to aid in transfer of the tissue specimens through the various process steps.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is an enlarged, exploded view of a first cryodisc for use with the rotary motion platforms and a sealing ring thereof.

FIG. 3 is a fragmentary side elevation of the cryodisc shown in FIG. 2 with a portion broken away to show detail thereof and including a portion of the apparatus of FIG. 1 disposed on either side of the cryodisc shown in cross-section.

FIG. 5 is a fragmentary cross sectional view taken along the line 5-5 of FIG. 3.

FIG. 6 is a fragmentary cross sectional view taken along the line 6-6 of FIG. 5.

FIG. 12 is an enlarged, partial, and somewhat schematic cross-sectional view taken along the line 12-12 of FIG. 1, showing the object holder tray in an open position.

FIG. 13 is an enlarged partially schematic cross-sectional view similar to FIG. 12 showing the object holder tray in a closed position.

FIG. 15 is a partially schematic top plan view of the cryodisc of FIG. 2 shown with three frozen tissue specimens, identification labels and in the process of being covered with embedding medium.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
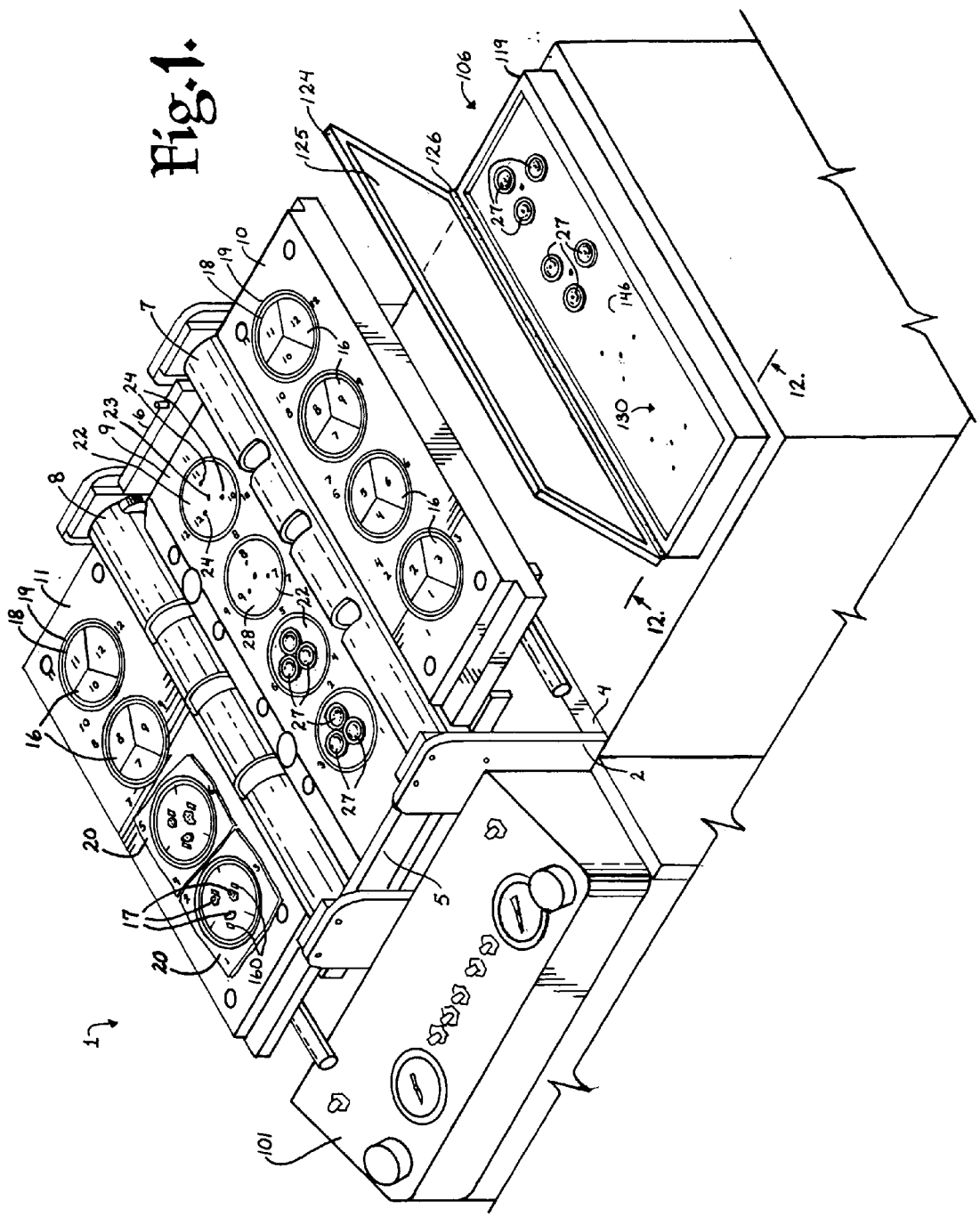
FIG. 1 is a fragmentary perspective view of a tissue freezing apparatus according to the present invention including two tissue-receiving rotary motion platforms, each including four cryodiscs, two of the cryodiscs each shown with three tissue samples and accompanying identification labels; a central platform equipped with four cryodiscs, two shown with three object holders mounted on each cryodisc; and a box and moistening tray shown with six object holders thereon.

An apparatus generally indicated by the reference numeral 1 for preparing frozen tissue specimens in accordance with the present invention is depicted in FIGS. 1-16, and includes a platform mechanism 2 and a fluid transfer system 3. With reference to FIG. 1, the platform mechanism 2 includes a base 4 supporting fixed, upstanding front and rear support panels 5 and 6. The panels 5 and 6 support between them a pair of laterally spaced, generally horizontal columns 7 and 8 in vertically spaced relation to the base 4. A central linear motion platform 9 is located between the support panels 5 and 6 and is supported on the base 4 by well known structure permitting the platform 9 to be raised and lowered in spaced relation to the base 4. The support columns 7 and 8 are coupled with respective rotary motion platforms 10 and 11 in laterally spaced relation to the central platform 9 and in vertically spaced relation to the base 4. The columns 7 and 8 are pivotally coupled with the support panels 5 and 6, permitting selective axial rotation of the columns 7 and 8 and the respective rotary motion platform 10 and 11 from an open position, in which the platform 10 or 11 is laterally adjacent to the central platform 9, to a covering position, in which the platform 10 or 11 is vertically adjacent the central platform 9.

Figure 9:
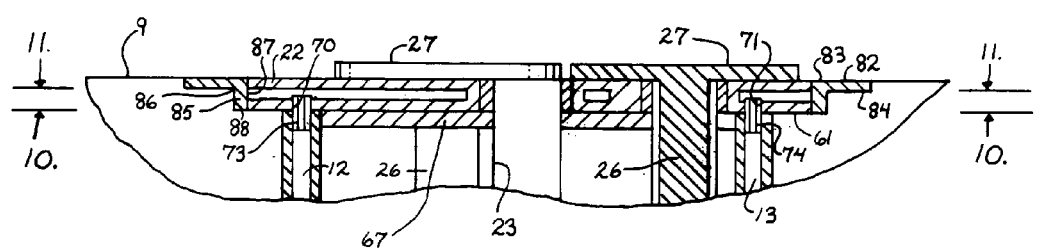
FIG. 9 is a cross-sectional view taken along the line 9-9 of FIG. 8.

In addition to the respective rotary motion platforms 10 and 11, the columns 7 and 8 also support associated components of the fluid transfer system 3, best shown partially schematically in FIGS. 6 and 9. The fluid transfer system 3 includes flexible cryogen supply conduits 12, which are coupled with a source (not shown) of a liquid cryogenic material, such as liquid nitrogen, and return conduits 13. While the illustrated embodiment is designed for use with liquid nitrogen because it is generally inert and non-combustible, the apparatus 1 may be used in conjunction with other cryogenic fluids.

Figure 14:
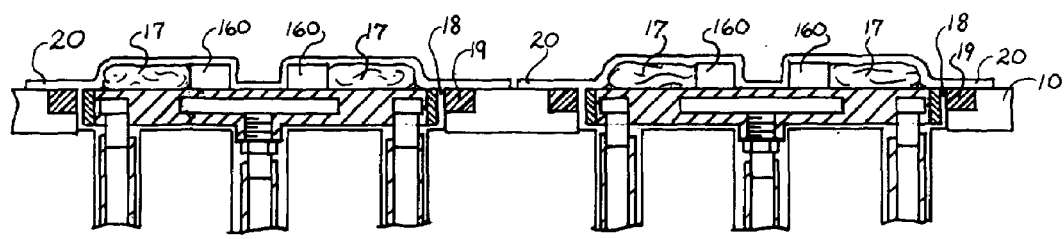
FIG. 14 is a cross-sectional view similar to FIG. 6, showing two cryodiscs each, with two tissue specimens and adjacent identification labels, all covered with a plastic membrane.
Figure 16:
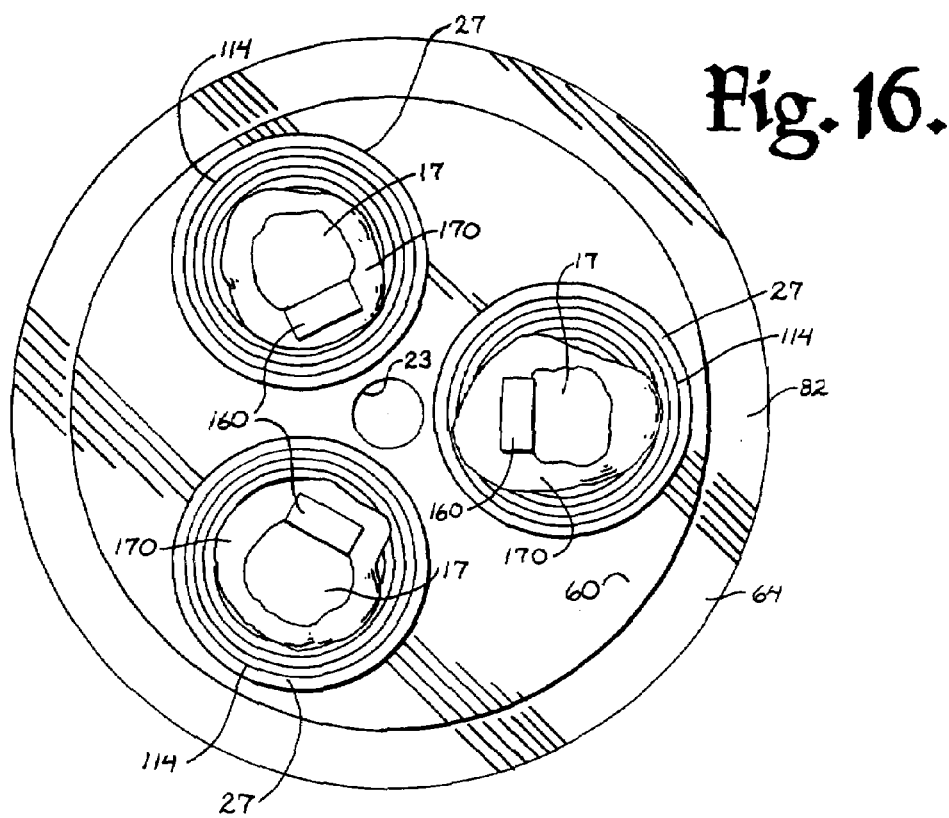
FIG. 16 is a partially schematic top plan view of the frozen tissue specimens and identification labels of FIG. 15 shown transferred to the object holders of FIG. 8 during a process of the invention.

With reference to FIGS. 1-6 and 14, each of the rotary motion platforms 10 and 11 includes a series of four spaced cryodiscs 16 (designated "rotary" cryodiscs, for clarity) for receiving tissue specimens 17. Each rotary cryodisc 16 is also encircled by a groove 18 that is in fluidic communication with a vacuum pump (not shown). Encircling a periphery of each groove 18 is a groove 19 filled with a pressure sensitive adhesive. A sheet of a plastic film 20 is supplied for placement over one or more specimens 17 placed on each cryodisc 16 as shown in FIG. 1 in covering relationship to the grooves 18 and 19, and a vacuum is drawn through the groove 18. The adhesive-filled grooves 19 allow for quick and ready placement and attachment of the plastic film 20 to the platform 10 or 11 and further provides a seal between the platform 10 or 11 and the film when vacuum is pulled through the grooves 18. As shown in FIG. 14, the vacuum then serves to draw the film sheet 20 tightly against the specimen or specimens 17, the cryodisc 16 and the surface of the rotary motion platform 10 or 11. In this manner, the plastic film 20 compresses the specimens 17 against the cryodisc 16 and air pockets between the specimens 17 and the cryodisc 16 are drawn radially outward and removed by the vacuum.

The grooves 19 are preferably filled with a pressure sensitive adhesive that is first melted and poured into the grooves 19. Such an adhesive adheres to the plastic film 20 but allows for easy removal of the film 20. Although vacuum grease may be utilized to provide a seal between the film 20 and the platforms 10 or 11, a pressure sensitive adhesive is preferred as it is not necessary to replace the adhesive each time the apparatus 1 is used. A preferred pressure sensitive adhesive is produced by the HB Fuller Company under the product designation HM1478. Alternatively, rubber cement or white rubber may be utilized in the grooves 19.

In an alternative embodiment, a single adhesive groove (not shown) extends along a periphery of each of the platforms 10 and 11, surrounding all four cryodiscs 16 on the platform 10 or 11. Such a groove allows for the placement of one large sheet of plastic film (not shown) over all of the tissue specimens on all four cryodiscs 16 of a platform 10 or 11, rather than the placement of smaller individual plastic sheets over each cryodisc 16.

With particular reference to FIGS. 1 and 2, in order to easily identify tissue specimens and track such specimens during processes of the invention, each cryodisc 16 is separated into three equal sections. A top surface 21 of the cryodisc 16 is divided into three sections by equidistant radially extending lines 21*a*, 21*b* and 21*c*. The lines 21*a*, 21*b* and 21*c* may be made by engraving and then filling with a bright colored paint. The three sections formed by such lines have a numeral from one to twelve engraved or otherwise imprinted on both the individual section and on the platform 10 or 11 adjacent the particular section to aid in identification when the individual sections are covered with a tissue specimen 17.

With reference to FIGS. 1 and 7-11, the linear motion platform 9 has four cryodiscs 22 somewhat similar to the rotary cryodiscs 16 that are sized and spaced to cooperate with the rotary cryodiscs on the rotary motion platforms 10 and 11. The cryodiscs 22 are designated herein as linear cryodiscs 22 to distinguish from the rotary cryodiscs 16. Formed in each cryodisc 22 are a central hollow bore 23 and a plurality of evenly spaced peripheral hollow bores 24. In the illustrated embodiment there are three evenly spaced hollow bores 24 located outwardly radially from the central hollow bore 23. Each of the bores 23 and 24 are sized for receiving a stem 26 of a tissue-receiving plate or object holder 27, best shown in FIGS. 1, 8 and 9. The bore 23 provides for the use of a single larger object holder (not shown) accommodating a larger tissue specimen (not shown). In the illustrated embodiment, three object holders 27, each accommodating a smaller tissue specimen 17 may be placed on each cryodisc 22.

Figure 7:
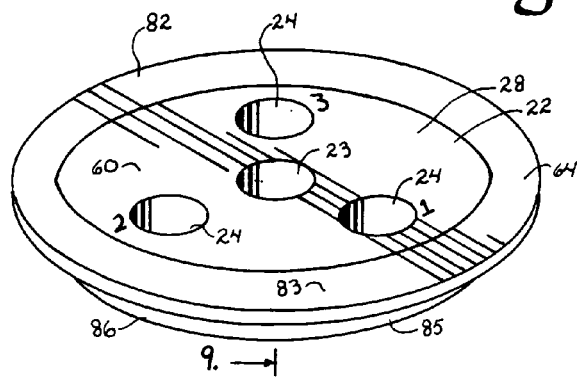
FIG. 7 is a perspective view of a cryodisc for use with a linear motion platform, showing a sealing ring thereof in place.
Figure 8:
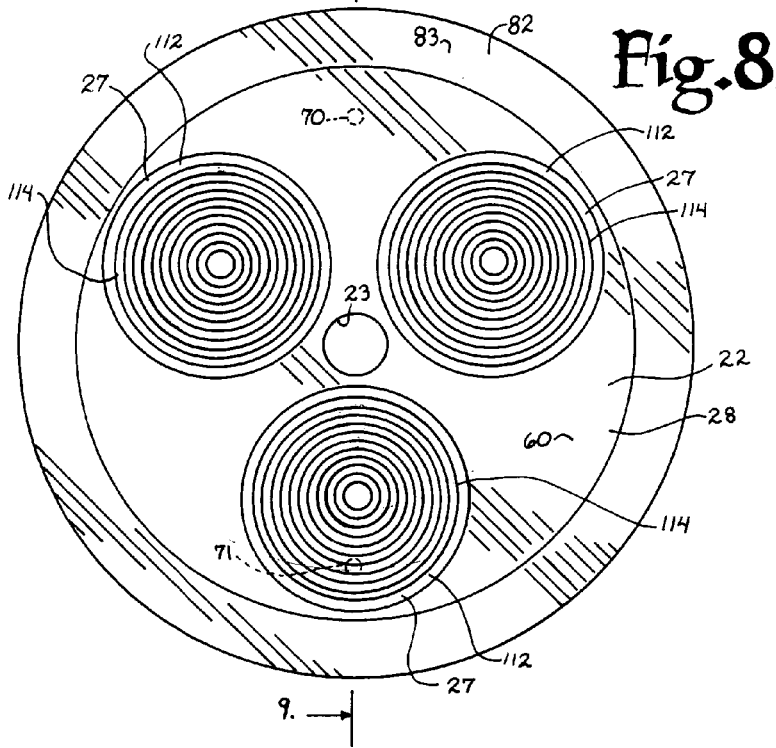
FIG. 8 is an enlarged top plan view of the cryodisc of FIG. 7, shown with three object holders mounted thereon.

With particular reference to FIGS. 1 and 7, in order to easily identify tissue specimens and track such during processes of the invention, a top surface 28 of the four linear motion cryodiscs 22 and the platform 9 are marked with the numerals one to twelve, cooperating with placement of such numerals on the platforms 10 and 11, so that a tissue specimen placed, for example, on a section identified with the numeral "5" of the cryodisc 16 is transferred to an object holder 27 at an area of a cryodisc 22 also identified, for example, with the numeral "5".

Returning to a description of the rotary platform cryodiscs 16, illustrated in FIGS. 2-6, each disc 16 includes the top or upper surface 21 that is substantially circular, a substantially circular bottom or lower surface 31 and an annular circumferential sealing ring or seal 33 extending between the surfaces 21 and 31. Each cryodisc 16 is equipped with a channel system, generally 34, for circulation throughout the cryodisc 16 of a cryogenic fluid delivered via the fluid transfer system 3. The illustrated cryodisc top surface 21 is generally planar and smooth, for receiving the tissue specimens 17. The rotary cryodisc top surface 21 is preferably coated with a polymeric composition, especially a tetrafluoroethylene, such as is sold under the trademark Teflon® by Du Pont, to facilitate quick release of the specimens 17. The bottom surface 31 is also generally planar and smooth and includes a central stem 38 that is apertured to provide an inlet port 39 for coupling with the supply conduit 12 through a nipple 40. The bottom surface 31 also includes a pair of circumferentially spaced apertures or outlet ports 41, for coupling with the return conduits 13 by means of nipples 42. The sealing ring 33 also includes a top or upper surface 43 and a bottom or lower surface 44 with a sidewall 45 therebetween.

The top and bottom surfaces 21 and 31 of the cryodisc 16 are illustrated in FIGS. 2 and 5 as substantially circular in shape and identical in diameter, with the sealing ring 33 sized to encircle the disc sidewall 32 in snug or generally sealing relationship. The sealing ring top and bottom surfaces 43 and 44 are aligned so as to be contiguous with and extend generally flush with respect to the cryodisc 16 top and bottom surfaces 21 and 31 respectively.

Figure 4:
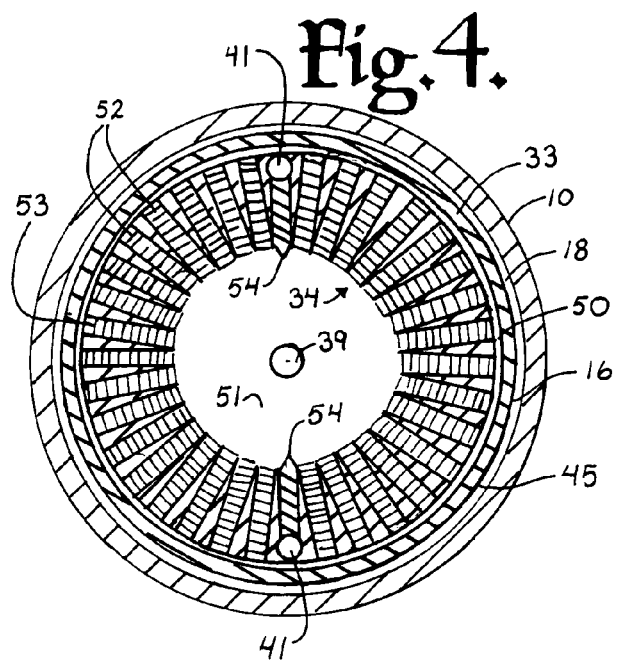
FIG. 4 is a fragmentary cross sectional view taken along the line 4-4 of FIG. 3.
Figure 10:
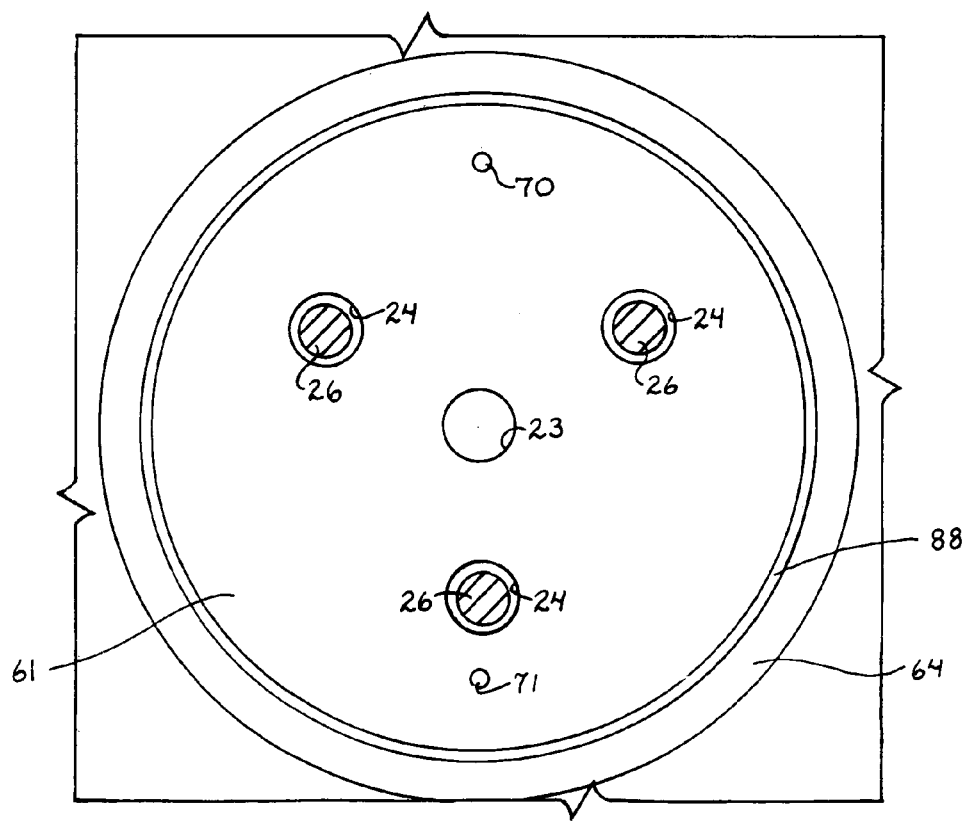
FIG. 10 is a cross-sectional view taken along the line 10-10 of FIG. 9.

As illustrated in FIGS. 3, 4 and 6, each rotary cryodisc 16 includes the channel system 34 that has a circular manifold configuration for circulation of a cryogenic fluid throughout the cryodisc 16. The channel system 34 includes a circumferential groove or perimeter channel 50 and an axial reservoir area or collection chamber 51 which is concentric with the inlet port 39. A series of spaced radial, but centrally converging, bores or channels 52 communicate between the circumferential channel 50 and the reservoir 51. The radial channels 52 are each equipped with a series of spaced and radially inward projecting fins, ridges or serrations 53 for operably increasing turbulence in the cryogenic fluid and enhancing heat transfer from the cryodisc 16 to the cryogenic fluid. Two flow-directing dams 54 are provided to block the flow of cryogenic fluid directly from the reservoir 51 to the outlet ports 41.

The cryodiscs 22 disposed on the central linear motion platform 9 that are illustrated in FIGS. 7-11 each include a top or upper surface 60 and a bottom or lower surface 61. The bores 23 and 24 extend between the top and bottom surfaces 60 and 61. A sealing ring or seal 64 is configured for mated sealing engagement with the cryodisc 22 about a circumference thereof, sealing at both the top and bottom surfaces 60 and 61. Each cryodisc 22 also is equipped with a channel system 65 somewhat similar to that of the rotary platform cryodiscs 16 and used for circulation of the same cryogenic material delivered via the fluid transfer system 3. The apparatus 1 may also be equipped with a heating element 67 disposed beneath the cryodiscs 22 near the bottom surface 61 and controlled by a thermostat (not shown), for warming the cryodiscs 22 to a desired temperature after usage, so as to be ready for a next usage.

The cryodisc 22 top surface 60 is generally planar and smooth, for supporting the tissue receiving object holders 27 and providing maximum thermal contact for heat transfer between the object holders 27 and the cryodisc 22. Peripherally spaced inlet and outlet ports 70 and 71 respectively, communicate with the channel system 65 and couple with respective supply and return conduits 12 and 13 via respective nipples 73 and 74. As shown in FIGS. 7 and 9, the sealing ring 64 is generally L-shaped when viewed in cross-section including a radially outward extending upper flange portion 82 having upper and lower surfaces 83 and 84, respectively, and a lower, disc-circumscribing portion 85 having an outer sidewall or skirt portion 86, an inner sidewall 87, and a lower or bottom surface 88 therebetween.

The top and bottom surfaces 60 and 61 of the linear cryodisc 22 are generally circular in shape and identical in diameter, with the sealing ring 64 sized to encircle the disc 22 in substantially sealing relationship with the sealing ring flange upper surface 83 aligned to form a contiguous surface with the disc top surface 60 and the sealing ring lower portion bottom surface 88 aligned to form a substantially flush, contiguous surface with the disc bottom surface 61. This construction permits the top surface 60 of the cryodisc 22 to extend radially outwardly beyond the lower portion 85 of the seal 64. In this manner, the mass of the cryodisc 22 to be cooled is reduced in proportion to the size of the usable surface, thus minimizing the quantity of cryogenic fluid necessary to lower the temperature of the cryodisc 22 and the tissue specimen 17. While the upper flange 82 and the lower portion 85 are depicted herein as being of unitary construction, it is foreseen that the flange portion 82 may be of unitary construction with the top surface 60 of the linear disc 22, with the lower portion 85 serving as a sealing ring. It is also foreseen that the shape of the top surface 60 including the flange portion 82 when viewed from above may be altered to a non-circular configuration, such as for example, triangular or other multilateral, ellipsoid or eccentric shape.

Figure 11:
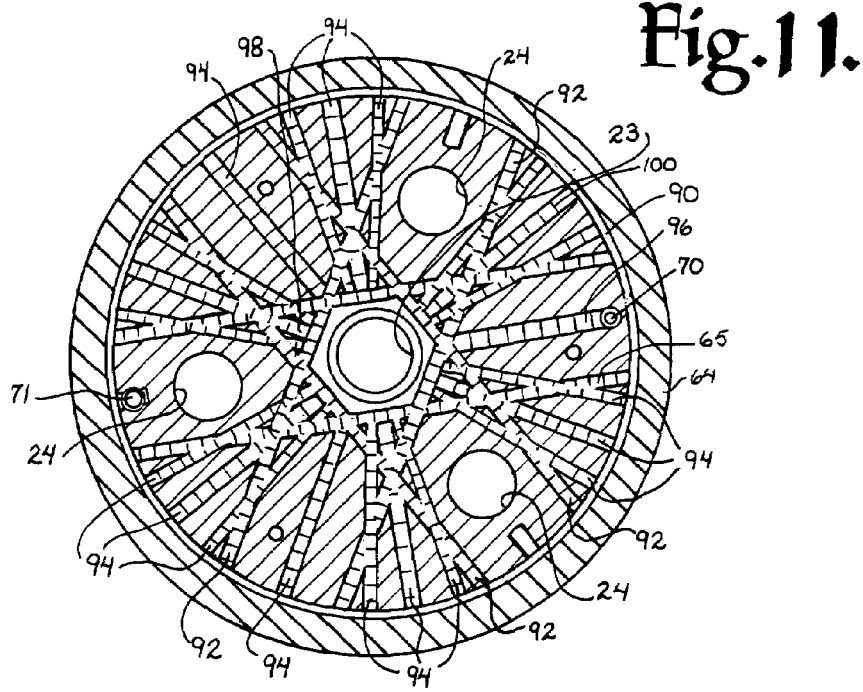
FIG. 11 is a cross-sectional view taken along the line 11-11 of FIG. 9.

The channel system 65 illustrated in FIGS. 9 and 11 includes a substantially circular, circumferential, perimeter groove or channel 90, a plurality of intersecting chordal channels 92 flow connected to the perimeter channel 90 at both ends thereof, and radial channels 94 extending from near the bore 23 to the perimeter channel 90. Specifically, pairs of chordal channels 92 flow on either side of each of the bores 24. A group of three adjacent radial channels 94 flows outwardly from a central area of each of the chordal channels 92. There is also a radial channel 94 evenly spaced between each of the three bores 24, one of which is an inlet channel 96 directly flow connected to the inlet port 70. The intersection of the chordal 92 and radial 94 channels near the center bore 23 creates an axial reservoir area or collection chamber 98 that surrounds the bore 23. The inlet channel 96 that is directly flow connected to the inlet port 70 is also directly flow connected to the collection chamber or area 98, but not directly connected to the outer or perimeter channel 90. The outlet port 71 is directly flow connected to the outer channel 90, but not directly flow connected to the collection chamber or area 98. Similar to the channel system 34 of the rotary cryodisc 16, the channels 92 and 94 may be equipped with spaced fins, ridges or serrations 100 for producing turbulence and enhancing heat transfer.

The cryodiscs 16 and 22 are both preferably constructed of a material having a high coefficient of heat transfer, such as a metal, with aluminum being particularly preferred. The circumferential sealing rings 33 and 64 are preferably constructed of a heat-shrink aluminum alloy to ensure a tight seal between the discs 16 and 22 and their respective rings 33 and 64. Any other suitable thermally conductive material may also be employed. The channel systems 34 and 65 are preferably constructed by drilling, although it is foreseen that they may also be of cast or molded construction. The fins 53 and 100 are formed by threading or tapping, or by other suitable means.

While the outstanding upper flanges 82 of the sealing rings 64 for use with the linear platform cryodiscs 22 advantageously reduce the thermal mass of the cryodiscs 22 to be cooled, it is foreseen that the rings 64 may be constructed without the flanges 82, with a structure similar to the sealing rings 33 for use with the rotary cryodiscs 16. It is also foreseen that the sealing rings 33 for use with the rotary cryodiscs 16 may be constructed to include flange structure similar to the flanges 82.

In use, a quantity of liquid nitrogen or other cryogenic fluid is conveyed via the supply conduits 12 from a storage vessel (not shown) to the inlet ports 39 and 70 of the cryodiscs 16 and 22. In the case of the rotary motion platform cryodiscs 16, the supply conduit 12 conveys the liquid nitrogen through the inlet port 39 and into the axial reservoir 51. The nitrogen flows outwardly from the reservoir 51, into the radial channels 52, where it passes over the fins 53. The fins 53 cause turbidity in the flow, which enhances heat transfer from the structure of the cryodisc 16 to the liquid nitrogen. Portions of the liquid nitrogen encounter the flow-directing dams 54, that prevent the liquid from exiting directly from the outlet ports 41. Nitrogen gas flows into the perimeter channel 50, which is sealed by the sealing ring 33 to prevent escape of gas or liquid to the atmosphere. The nitrogen gas travels around the perimeter channel 50 until it reaches the outlet ports 41, where the gas is conveyed away via return conduits 13.

A portion of the supply conduit system 12 also conveys a quantity of liquid nitrogen from the storage vessel (not shown) to each inlet port 70 of the linear platform cryodiscs 22. The fluid travels through the inlet channel 96 to the central reservoir area 98 that surrounds the central bore 23 and outwardly through the chordal and radial channels 92 and 94. As the liquid nitrogen warms and gasifies, nitrogen gas passes outwardly from the perimeter channel 90 through the outlet port 71 and is conveyed away via the return conduits 13.

A control panel 101 is mounted on the front of the apparatus 1 for use by an operator in control and use of the apparatus 1. An object holder moistening tray, generally 106, may be mounted on or placed near the apparatus 1 for ready access to the object holders 27.

The moistening tray 106 illustrated in FIGS. 1, 12 and 13 holds up to twelve small object holders 27 (six are shown) that cooperate with the three peripheral bores 24 formed in each of the linear platform cryodiscs 22. Alternatively, the moistening tray 106 may be used to hold four larger object holders (not shown) that cooperate with the central bore 23 of each of the linear platform cryodiscs 22. Whether the object holder 27 or a larger object holder (not shown) is utilized, the moistening tray 106 allows for ready access to object holders moistened with isopropyl alcohol on underside surfaces 108 thereof.

In the illustrated embodiment, each object holder 27 includes the previously identified stem 26 thereof that is substantially cylindrical in shape and a circular plate 110 having a top surface 112 and the afore mentioned underside surface 108. Formed in the top surface 112 are circular concentric grooves 114 that aid in holding a frozen tissue specimen 17 as will be described in more detail below. The stem 26 protrudes centrally from the plate 110 underside surface 108 and is integral or otherwise attached thereto. The illustrated object holders 27 have plates 110 that are approximately 40 mm in diameter, but may be larger or smaller, depending on the preference of the user and relative size of cooperating equipment. The illustrated embodiment provides for the rapid freezing of up to twelve tissue specimens 17 during a single freezing cycle of the apparatus 1. The object holder stem 26 is also sized and shaped to cooperate with an apparatus (not shown) for holding the object holder 27 during slicing of the frozen tissue specimen 17 in preparation for microscopic examination.

The illustrated moistening tray 106 is a rectangular container having a box-like body 119 that includes a base 120 and side walls 122, and further includes a rectangular lid 124 with a glass window 125 and a hinge 126 attaching the lid 124 to the body 119. Within the container body 119 is an object holder holding and elevating structure, generally 130, that includes a platform structure 132 having spaced bores 134 formed therein; a plurality of rods 136 attached to the platform structure 132 with springs 138; a pair of elongate bars 140 slidable with respect to the platform structure 132, each having sloping, curved surfaces 142 formed therein for operable engagement with the spring-loaded rods 136; a pair of levers 144 cooperating with both the slidable bars 140 and the lid 124; and a moistening pad 148 saturated with alcohol, preferably 70% isopropyl alcohol, the pad 148 having spaced apertures 150 cooperating with the bores 134.

The platform structure 132 fits snugly within the box-like body 119. In the illustrated embodiment, the structure 132 is of substantially solid construction, with the exception of the bores 134, two lower substantially horizontal spaced grooves 150 sized and shaped for receiving the sliding bars 140, the grooves partially defined by an end wall or stop 151; and grooves (not shown) perpendicular to the grooves 150 for receiving the rods 136 and springs 138. The bores 134 and the pad apertures 148 are each sized to receive the stem 26 of an object holder 27, with the underside 108 thereof in contact with the moistening pad 146 when the box is closed as shown in FIG. 13. The bores 134 and the rods 136 are aligned such that when an object holder 27 is placed in any bore 134, the stem 26 contacts a rod 136. When the moistening tray 106 is in an open position as shown in FIG. 12, the rods 136 are pulled upwardly in a direction toward the moistening pad 146 by the springs 138 that are attached to an upper portion of the structure 132. In such an open position, the rods 136 seat in an upper notch 152 of the sliding bars 140. When the lid 124 is manually closed as shown in FIG. 13, the lid 124 makes contact with the levers 144, pressing the levers 144 in a downward direction, causing the levers to pivot about a pivot pin 153 and thereby press against the sliding bars 140, causing the bars 140 to slide in a horizontal direction toward the stop 151 which in turn causes the rods 136 to slide along the curved surfaces 142, expanding the spring and moving the rods downward toward the base 120 to a closed position seated in a lower notch 154 of the sliding bars 140. When the lid 124 is completely closed, the object holders 27 are fully seated in the platform structure 132 with the undersides 108 thereof contacting the moistening pad 146. When the lid 124 is opened, the tension on the rods 136 pulled by the springs 138 lifts the rods 136 and engaged object holders 27 upwardly, lifting the plates 110 of the object holders 27 up and away from the moistening pad 146 for easy grasping by a user. Furthermore, the spring-loaded construction of the structure 130 is flexible to provide for manual pressing of an object holder plate 110 down onto the pad 146 when the tray is in the open position shown in FIG. 12, thereby lowering the rod 136 and providing for re-wetting of the object holder underside 108 prior to installation of the object holder 27 on the cryodisc 22. As shown in FIG. 12, the bores 134 are formed such that when the tray 106 is in the open position of FIG. 12, the object holders 27 are elevated with the plates 110 slightly tilted, making the object holders 27 easier to grasp.

Preferably, the moistening pad 146 is saturated with 70% isopropyl alcohol. Furthermore, a sodium chloride solution may be added to the isopropyl alcohol, and the resulting mixture utilized to saturate the moistening pad 146. When an object holder 27 wetted with the isopropyl alcohol/sodium chloride mixture is placed onto a frosted linear cryodisc 22, the linear motion platform 12 elevates and contact is made between the lower, wetted surface 108 of the object holder 27 and the upper surface of the frosted cryodisc 60. Advantageously, consistent and extremely rapid heat transfer occurs between the tissue object holder 27 and the cryodisc 22.

Figure 17:
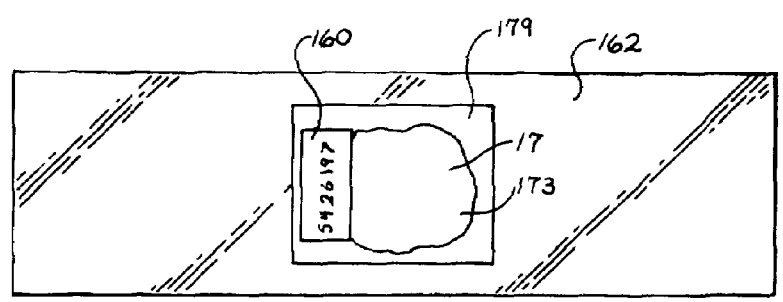
FIG. 17 is a partially schematic view of a sliced tissue specimen and identification label shown on a glass slide during a process of the invention.

As previously discussed herein, tracking of tissue specimens 17 during processes according to the invention is aided by engraving or otherwise placing coordinating identifying numerals on and near the cryodiscs 16 and 22. Further tracking may be accomplished by the use of a labeling system that includes small discs with micro numbers and/or letters and/or corresponding bar codes, shown as micro-labels 160 in FIGS. 1 and 14-17. Each micro-label 160 is packaged with accompanying identically numbered or otherwise marked macro-labels or dots that may be secured by an operator to the name area of an examination slide as well as to report and log books. A bar code or a set of numbers and/or letters are embedded throughout a full thickness of the label 160 so that when the frozen specimens 17 are sliced, a slice of precise information also accompanies the tissue specimen onto a glass examination slide 162 as illustrated in FIG. 17. When the microscopist examines the tissue specimen 17, the micro-label 160 with a number, letters or bar code is visualized and manually recorded or may be recognized by a scanner. For multiple specimens from one patient, discs may be available that represent different sub-units. Such can be detected, for example, by using lower case letters or numbers with different fonts. It is foreseen that such micro-labels 160 may be utilized with permanent tissue specimens as well as with the frozen specimens 17 according to the present invention. The micro-labels or discs 160 are preferably made from a protein substance that adheres well to glass slides and more preferably of a stained protein using silver, using known micro-printing technology with ink preferably reinforced with silk or other protein, such as that found in spider webs, to provide stability during slicing and viewing. Moisture barrier packaging for the micro-labels 160 is preferred that maintains the labels 160 in a desired moisture range for ease in slicing. Macro-labels may be packaged adjacent the protein disc 160 and be of sufficient quantity to label glass slides, reports, and/or log books.

During a process according to the invention, which will be described in greater detail below, tissue specimens 17 are initially frozen on the rotary platform cryodiscs 16 and then preferably covered with a viscous, fiber-reinforced embedding medium 170, followed by transfer the to object holders 27 disposed on the linear platform cryodiscs 22. Furthermore, an amount of a standard embedding medium, such as O.C.T. compound (not shown), is preferably placed on the object holders 27, filling in the grooves 114 thereon prior to transfer of the frozen tissue specimens 17 onto the object holder 27. O.C.T. is an abbreviation for "Optimal Cutting Temperature." O.C.T. is a well-known water soluble embedding medium for frozen tissue specimens, and for example, is sold under the mark TISSUE-TEK® by Sakura Finetechnical Co., Ltd., Tokyo, 103, Japan. The TISSUE-TEK® O.C.T. compound includes 10.24 weight percent polyvinyl alcohol; 4.26 weight percent polyethylene glycol; and 85.50 weight percent non-reactive ingredients (water).

As shown in FIG. 15, an applicator tube 172 is used to manually apply the fiber-reinforced embedding medium 170 onto the specimens 17. The embedding medium 170 is useful for holding the specimen 17 in place during slicing and transfer of a sliced specimen 173 to a glass slide 162 for review. A feature of the fiber-reinforced embedding medium 170 is that it adheres well to tissue specimens 17 and does not chip or break into chunks during the specimen slicing process.

A preferred fiber reinforced embedding medium for use according to the invention includes a mixture of (1) a known polyvinyl alcohol/polyethylene glycol embedding medium, such as the TISSUE-TEK® O.C.T. compound previously described herein; (2) fiber; and (3) an electrically conductive polymer. A particularly preferred embedding medium includes mixing the TISSUE-TEK® O.C.T. compound and the following: protein, preferably in the form of a silk fibers; cellulose, preferably bamboo cellulose; and polyaniline, preferably charged polyaniline. Another polyaniline for use according to the invention is a long chain polyaniline emeraldine salt grafted to lignin in a 20 wt. % dispersion in water (available from Sigma-Aldrich Corp., St. Louis, Mo.). It is believed that electrically conductive polymers such as polyaniline cross link with the cellulose fibers, forming a matrix or lattice therewith, providing control, hold and strength to the embedding medium. The following Example discloses a particularly preferred fiber-reinforced embedding medium 170.

EXAMPLE

| Component | Density (g/l) | Approximate Amounts (g) |
|---|---|---|
| Silk Fibers | | 0.1 to 5 |
| QC 200 Fiber[1] | >55 | 4 |
| QC 150 Fiber[1] | >160 | 1 |
| QC 90 Fiber[1] | >170 | 1 |
| Ball ® Fruit Jell ® Pectin[2] | | 2 |

[1]QC Fiber is a product designation for bamboo-fiber available from Crea-Fill Fibers Corp., 10200 Worton Road, Chesterown, MD. The numerals 200, 150, and 90 designate grades, primarily indicating density and particle size ranges.
[2]Registered trademarks owned by Jarden Corp. for powdered mixture of sucrose, dextrose and citric acid.

The above ingredients were mixed and folded into the following mixture at 60° C.:

| Component | Approximate Amounts |
|---|---|
| polyaniline (water soluble) | 0.5 to 50 mg |
| O.C.T. compound[3] | 100 ml |

[3]TISSUE-TEK ® O.C.T. (10.24 wt. % polyvinyl alcohol; 4.26 wt. % polyethylene glycol; 85.50% water).

Figure 18:
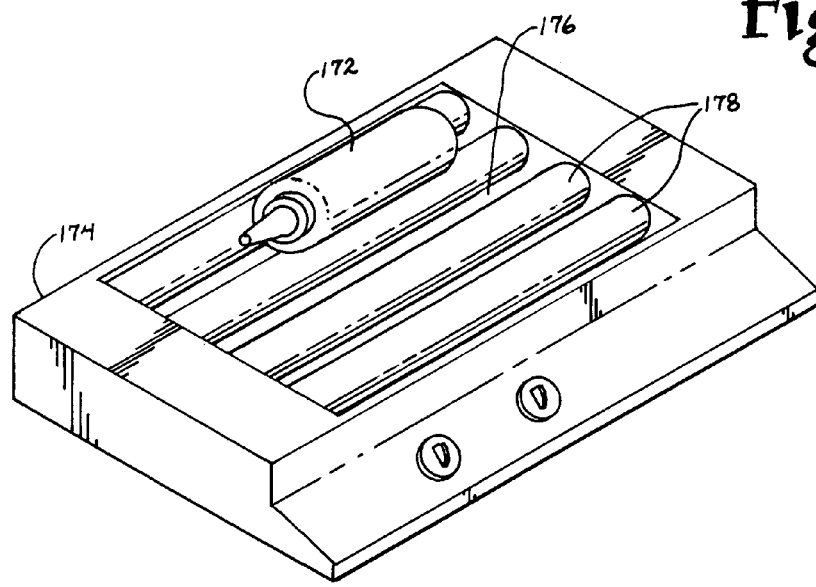
FIG. 18 is a perspective view of an embedding medium heating unit according to the invention shown with an application tube.

To enhance adhesion between the tissue specimens 17 and the fiber-containing embedding medium 170, it is helpful to warm the applicator tube 172 filled with the medium 170 on a heating device, such as the heated roller mixer 174 shown in FIG. 18. The device 174 is generally of known construction in the cooking arts and includes a heating element 176 disposed beneath rotating rollers 178. Preferably, the roller mixer 174 mixes the medium 170 and heats the medium 170 to a temperature range of 25° C. to 65° C.

A process for the surgical removal of tissue specimens and preparation for histologic examination according to the invention is set forth in the following steps. Although the process is described with respect to a single tissue specimen 17, it is noted that for the illustrated embodiment of the apparatus 1, up to twelve specimens 17 may be processed during a single cycle of the apparatus 1. Initially, a tissue specimen 17 is excised as a truncated sphere; desirably including an entire tumor to be removed. The specimen 17 is then relaxed by cutting on the skin side, which is a partial sphere, to relax and flatten the specimen. Next, four corners of the specimen 17 are marked with blue, green, red and orange dye to make it possible to identify the orientation of the specimen 17 relative to the patient's wound. A description or other record is kept of the orientation of the wound with respect to the patient and the specimen 17 and where the dye is placed.

The relaxed and dyed specimen 17 is then placed on the surface 21 of a rotary platform cryodisc 16 with the skin side facing up and away from the surface 21. A micro label 160 is placed next to the specimen 17. Plastic film 20 is then placed over the specimen 17 and the micro label 160 is moved and pressed against the specimen 17, with the specimen 17 being manually urged to a substantially flat orientation on the surface 21. The film 20 is also manually pressed against the adhesive filled groove 19. A vacuum is drawn through the groove 18 to about 27 mm Hg under the film 20 to snug the specimen 17 and accompanying micro label 160 against the surface 21 of the cryodisc 16. With reference to FIG. 14, such a vacuum process is shown being applied to two specimens 17 on each cryodisc 16, each with an adjacent micro label 160 and covered with a plastic film 20.

A quantity of cryogenic fluid is then circulated throughout the fluid transfer system 3 in the rotary and linear cryodiscs 16 and 22, as previously described. Circulation of the liquid chills the rotary discs 16 to a preferred temperature, that varies depending upon the preference of the technician, but is typically between about −30° C. and about −50° C., and more preferably between about −40° C. and about −50° C. It takes between about thirty to about forty-five seconds for the discs 16 to cool to the desired temperature.

When the specimen 17 starts to freeze, which is determined visually by change in appearance, the film 20 is carefully peeled away. Then, fiber reinforced embedding medium 170 is squeezed from a tube 172 directly and firmly against and around the frozen specimen 17 and the micro label 160.

The object holder moistening tray 106 is then opened and an object holder 27 having an underside 108 wetted with isopropyl alcohol or an isopropyl alcohol sodium chloride mixture, is placed on the cryodisc 22. A light or very thin coat of less viscus embedding media, such as the standard embedding medium (O.C.T. Compound) previously described herein, is placed on the object holder plate 110 to fill grooves 114 therein. Alternatively, the standard embedding medium is applied on top of the fiber reinforced embedding medium 170 that covers the specimen 17.

The moistened object holders 27 are placed in respective bores 24 with the object holders 27 somewhat spaced from the surface of respective cryodiscs 22 until the platform 10 or 11 is rotated from a position lateral to the platform 9 to a covering position and the respective cryodisc or cryodiscs 16 with the frozen specimen or specimens 17 thereon each engage a respective object holder 27 at which time the engaged object holder 27 drops and comes in touching contact with the top surface 60 of the cryodisc 22. In this manner, the object holder 27 becomes a near room temperature object holder engaging the cold specimen 17 which warms near the engagement and then is again quickly recooled when the object holder 27 engages the cryodisc 22. This aids in adhesion between the specimen 17 and the object holder 27, while the isopropyl alcohol cooperates with frost on the coating of the surface of the cryodisc 22 to enhance heat transfer and provide rapid and consistent cooling to the object holder 27.

The temperature of the combined object holder 27 and specimen 17 is adjusted according to the preference of the technician. The object holder 27 and specimen 17 are then placed in a slicing apparatus and sliced. Often ten to fifteen slices at about four microns each are taken until the technician is satisfied that the entire surface to be studied is represented.

Some technicians remove the embedding media 170 from the specimen 17 during slicing and then transfer the slice 173 to the slide 162 by means of an anti roll plate 179. The anti roll plate 179 helps prevent curling or rolling up of the specimen. Some technicians do not use the anti roll plate 179 and prefer to use the embedding media to drag the specimen slice 173 to the slide 162. In order to do this, the media must adhere to the specimen. This is accomplished by heating the fibrous embedding medium 170 first to between about 35° C. to about 65° C. on the heater 174. When the medium 170 touches the specimen 17 there is a quick thaw and then re-freezing that adheres the medium 170 to the specimen 17. In such case, the embedding media 170 serves a second transfer function in addition to the function of stabilizing the specimen 17 during slicing.

The specimen slice 173 is then examined by viewing the tumor margin surface area under a microscope. If tumor tissue is found in the studied slice 173, another tissue specimen is harvested and the process is repeated until the margins of the specimen 17 are completely free of tumor.

With particular reference to FIG. 15, a technician may prefer to place a relaxed and inked tissue specimen 17 on a small sheet of a polyester film, for example, a polyethylene terepthalate film sheet 182, such as provided under the trademark MYLAR® by Dupont Tejjin Films, to initially hold the specimen 17 on the rotary cryodisc 16, rather than placing the specimen 17 directly on the cryodisc 16. It is foreseen that an electrostatic (+) charged film, such as plasticized vinyl film, may also be used. The polyester film sheet 182 preferably has a thickness of 3 mils (0.003 inches equivalent to 0.0765 millimeters) and includes a slightly roughened surface finish on one side 184 thereof, suited for printing a grid or map thereon, and an opposite smooth side. The sheet 182 may include a pre-printed grid pattern or tissue orienting pattern as described more fully below with respect to a temporary tattoo according to the invention, including horizontal, vertical and radial lines with numerals identifying horizontal, vertical and radial locations and certain grid portions and numerals being printed in color, also as described with respect to the temporary tattoo. Additionally, the sheet 182 may include numerals to aid in the identification of the samples that coordinate with the numerals engraved or otherwise printed on the platforms 10 and 11 and the cryodiscs 16 and 22. The grid may be printed on the polyester sheet 182 with an ink or other substance similar to what is used for temporary tattoos, so that the grid pattern is transferable to the moist specimen surface, as described more fully below. Because the grid pattern and reference numeral printable substance does not readily transfer onto fat, preferably the reference numerals are repeated across a length of the grid design on the polyester sheet to ensure identification of a top surface of the frozen specimen with a reference numeral coordinating with the numerals engraved or otherwise printed on the platforms 10 and 11 and the cryodiscs 16 and 22.

The sheet 182 may be sized to fit on a cryodisc 16 such that all three specimens fit on a single sheet 182. In such a situation, three grid patterns may be printed on a single sheet 182. Alternatively, smaller sheets 182 may be used, one for each specimen 17, as illustrated on FIG. 15. In such a situation, a single grid pattern, such as that shown in FIG. 19, may be printed on each sheet 182. Furthermore, for certain procedures requiring large specimens, a larger sheet 182 may be used that is printed with a single grid pattern, similar to the pattern shown in FIG. 19. In such a usage, because the sheet 182 is larger, more detailed color coding and additional identifying numerals may be printed with the horizontal, vertical and particularly with respect to the radial grid lines, further aiding the process of locating and identifying tumor margin surfaces of interest. In particular, numerals may be printed about a circumference of a circular design having a plurality of horizontal and vertical lines and identifying radial lines with respect to a color coded X and Y axis (as described herein with respect to the pattern 190 shown in FIG. 19). The segments formed by the radial lines are identified by numerals printed about the circumference of the design in both degrees and in the clock-wise fashion described herein with respect to the pattern 190 shown in FIG. 19. Depending on the size of the sheet 182, the radial segments may be identified along the design circumference in segments of fifteen degrees each, corresponding to thirty minute increments. The numerals located about the design circumference may also be printed or shaded with the same color coding as described herein with respect to the X and Y axis of FIG. 19.

Preferably, the sheet 182 is prepared for use according to the invention by brush coating with a natural protein, such as egg albumin on the slightly roughened and possibly printed surface 184. It is foreseen that other types of materials that have tissue adhesive or affinity properties may be used as coating material, including poly-L-lysine, aminoalkysilane, glycoproteins and gelatin. Although not required, a technician may also desire to score the opposite, smooth side of the sheet 182, most preferably with some of the scores extending completely through the sheet 182. A drop or other small amount of the standard embedding medium previously described herein is first placed centrally on a section of the surface 21 of the cryodisc 16 where the specimen 17 will subsequently be placed. The sheet 182 is then placed on top of the standard embedding medium, with the smooth or scored side down and the tissue specimen 17 is placed on the side 184 of the sheet 182 coated with the albumin. The specimen 17 is then manually pressed against the sheet 182, the specimen 17 advantageously adhering to the surface 184. Alternatively, the specimen 17 is placed upon and pressed against the sheet 182 prior to placing the sheet 182 on top of the standard embedding medium on the cryodisc 16. Then, if desired, the operator may lift up the sheet 182 and view the specimen 17 underside through the substantially clear sheet 182, to ensure that edges of the specimen 17 are pressed against the surface 184 as desired by the operator. Photographs may also be taken of the specimen 17 through the film sheet 182 to further document and track the particular specimen. Thereafter, the sheet 182 with the specimen 17 thereon, are placed on the cryodisc 16, with the standard embedding medium disposed between the sheet 182 and the cryodisc 16 to temporarily secure the sheet 182 to the cryodisc 16 during subsequent rotation of the cryodisc 16 over to an object holder 27. Similar to the process steps previously described herein, a micro label 160 may be placed adjacent the specimen 17 and the specimen 17, label 160 and sheet 182 are then covered with a plastic film 20 and vacuum is pulled, followed by freezing of the specimen 17. The plastic film 20 is then removed and the fiber reinforced embedding medium 170 is applied on top of the frozen specimen 17 and accompanying label 160 as previously described herein. A standard embedding medium is then applied on top of the fiber-containing embedding medium 170 or, alternatively onto a selected, wetted object holder 27, removed from the moistening tray 106 and placed on a cooperating cryodisc 22. The embedded specimen 17 is then rotated and transferred to the object holder 27 on the cryodisc 22 as previously described herein. After transfer, a desired specimen temperature is reached and the polyester film sheet 182 is removed from the specimen 17. When the film sheet 182 has a grid pattern printed on it, any pattern or identification numeral printed on the film sheet 182 advantageously transfers to a top surface of the specimen 17, providing for additional identification and tracking as the specimen 17 is transferred from the cryodisc 22 to a slicing machine. The specimen 17 is then sliced and the sliced specimen 173 is reviewed.

Figure 20:
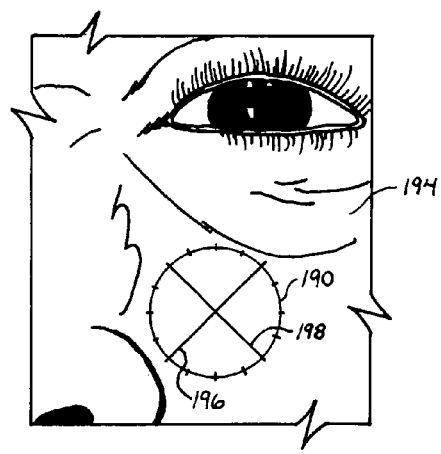
FIG. 20 is a partial front elevational view of a portion of a person's face shown with a temporary tattoo of the mapping pattern according to FIG. 19.
Figure 21:
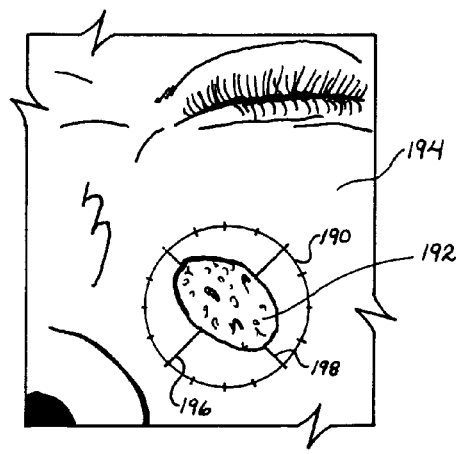
FIG. 21 is a partial front elevational view similar to FIG. 20, showing a portion of the mapping tattoo remaining after a tissue specimen has been harvested.
Figure 19:
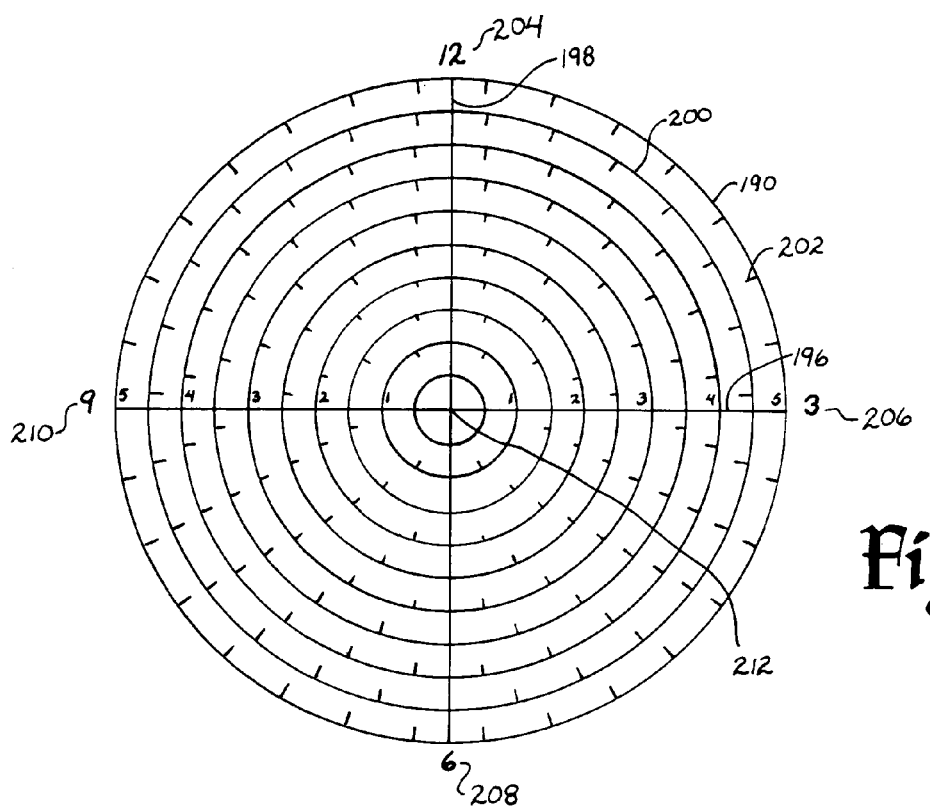
FIG. 19 is a top plan view of a tissue orienting or mapping pattern according to the invention.

In a process of the invention previously described herein, one of the method steps includes the marking of the specimen 17 with blue, green, red and orange dye to help identify the orientation of the specimen 17 relative to the patient's wound. With reference to FIGS. 19-21, such an orientation step is aided by the use of a tissue orienting pattern or grid illustrated as a temporary tattoo 190 in FIG. 19. The patterned temporary tattoo 190 is placed on the tumor-containing area of skin 192 of the patient 194, prior to harvesting the tissue specimen 17. The pattern 190 according to the invention shown in FIG. 19 includes an X axis 196, a Y axis 198 and a plurality of concentric circles 200. The circles include radial marks or ticks 202. The tissue orienting pattern 190 is further marked in a clock-wise fashion with a numeral "12" at a top 204 of the Y axis; a numeral "3" at an end location 206 on the X axis ninety degrees from the numeral "12"; a numeral "6" at a bottom 208 of the Y axis; and a numeral "9" at an end 210 of the X axis ninety degrees from the numerals "6" and "12" The X and Y axes of the pattern 190 are in color, with the Y axis portion extending from the center 212 to the numeral "12" being blue; the Y axis portion extending from the center 212 to the numeral "6" being in green; the X axis portion extending from the center 212 to the numeral "3" being in red; and the X axis portion extending from the center 212 to the numeral "9" being in orange. This color combination corresponds to the following standard practice of clock-wise marking of a specimen: blue at twelve o'clock; red at three o'clock; green at six o'clock; and orange at nine o'clock.

As illustrated in FIG. 21, after a tissue specimen 17 is harvested, a portion of the pattern 190 remains on the patient 194, clearly showing the X and Y axes, 196 and 198, respectively, and remaining concentric circles 200. The harvested specimen 17 is then inked at a top, bottom and either side thereof consistent with the tattoo 190 and is then frozen, sliced and examined as previously described herein. If further tissue removal is necessary, the tattoo pattern 190 remaining on the patient 194 then provides an accurate map for reorienting the specimen 17 with the patient and removing tissue from a desired area.

The pattern 190 may also be imprinted on the printable side 184 of the polyester sheet 182. The pattern or grid 190 allows a technician to precisely locate tumor roots on the tissue specimen 17 as the specimen 17 is pressed onto the sheet 182. Notations may then be made to allow for greater accuracy during reorientation after a respective specimen slice 173 is microscopically reviewed.

In a further aspect of the invention, known software may be utilized to create a digital contoured map of a floor and walls of a specimen 17 in order to improve accuracy during reorientation. For example, after a temporary tattoo 190 is applied to a patient 194 and a tissue specimen 17 is harvested, a first digital picture may be taken of the specimen 17 above the tissue and a second picture taken below the tissue, both pictures oriented with respect to the tattoo 190.

Then, a digital contour map is created for a periphery of the specimen 17, digitally compensating for any relaxing and flattening of the specimen 17. Pathologic notations made by the operator viewing the specimen slice 173 may be loaded into the compensated digital contour map. The compensated contour map is then digitally returned to the original specimen contour and then clinically reoriented to the tattoo 190 on the patient's wound area 192, indicating with greater accuracy the pathologic notation taken from the sliced specimen 173.

Temporary tattoos for use according to the invention are preferably polymer based. A preferred temporary tattoo 190 includes a polyvinyl alcohol resin mixed with linseed and mineral oils, obtainable from, for example, Johnson & Mayer, Inc., Hackensack, N.J.

It is to be understood that while certain forms of the present invention have been illustrated and described herein, it is not to be limited to the specific forms or arrangement of parts described and shown.

What is claimed and desired to be secured by Letters Patent is as follows:

1. In a cryogenic tissue freezing apparatus having a first cryodisc for receiving and quickly cooling a tissue specimen, the first cryodisc disposed on a rotatable platform for operably moving into a covering relationship with a second cryodisc disposed on a second platform, the improvement comprising:

a channel system disposed in the second cryodisc, the channel system in fluidic connection with a cryogenic system for circulation of a cryogenic fluid, the channel system including a peripheral channel and a plurality of intersecting chordal channels communicating with the peripheral channel.

2. The improvement of claim 1 further comprising a plurality of radial channels communicating with the chordal channels and the peripheral channel.

3. The improvement of claim 1 further comprising:
a) a plurality of evenly spaced bores extending through the second cryodisc disc, the chordal channels running on either side of each bore; and
b) a plurality of object holders, each object holder for receiving a frozen tissue specimen, each object holder receivable in one of the bores.

4. The improvement of claim 3 wherein the plurality of spaced bores includes a central bore and up to three peripheral bores.

5. The improvement of claim 3 further comprising a moistening tray for receiving the object holders and wetting undersides thereof with alcohol prior to placement of the object holders in the bores.

6. The improvement of claim 5 wherein the moistening tray includes a moistening pad and a holding structure, the holding structure having two positions, a first closed position wherein the object holders are received by the moistening tray with undersides thereof contacting the moistening pad and a second open position wherein at least a portion of the object holders are in spaced relation with the moistening pad.

7. The improvement of claim 1 wherein the rotatable platform has a groove surrounding the first cryodisc, the groove filled with a pressure sensitive adhesive.

8. In a cryogenic tissue freezing apparatus having a first cryodisc for receiving and quickly cooling a tissue specimen, the first cryodisc disposed on a rotatable platform for operably moving into a covering relationship with a second cryodisc disposed on a second platform, the improvement comprising:

a) a plurality of evenly spaced bores extending through the second cryodisc, each bore for receiving a stem of an object holder adapted for holding a tissue specimen thereon; and
b) a channel system disposed in the second cryodisc, the channel system in fluidic connection with a cryogenic system for circulation of a cryogenic fluid, the channel system including a peripheral channel and a plurality of intersecting chordal channels disposed between the bores and communicating with the peripheral channel.

9. The improvement of claim 8 further comprising a plurality of radial channels communicating with the chordal channels and the peripheral channel.

10. The improvement of claim 8 wherein the plurality of spaced bores includes a central bore and up to three peripheral bores.

11. The improvement of claim 8 including coordinating identification numerals placed on and near the first and second cryodiscs.

12. An apparatus for quick freezing a tissue specimen comprising:

a) a first platform member rotatable about an axis relative to a second platform member, the first platform member having at least a first cryodisc thereon and the second platform member having at least a second cryodisc thereon, the first and second cryodiscs for chilling by a cryogenic fluid, the first cryodisc being in a covering relationship to the second cryodisc when the first platform is rotated over the second platform, the first cryodisc divided into a plurality of sections, the second cryodisc having at least one bore cooperating with each of the sections of the first cryodisc;
b) a cryogenic system in operable fluidic connection with the first and second platform members;
c) a first channel system disposed in the first cryodisc including a first peripheral channel and a first set of radial channels communicating with the first peripheral channel; and
d) a second channel system disposed in the second cryodisc including a second peripheral channel and a plurality of chordal channels disposed between the bores and communicating with the second peripheral channel.

13. The apparatus of claim 12 wherein the second channel system includes a second set of radial channels disposed between the bores and communicating with both the chordal channels and the second peripheral channel.

14. The apparatus of claim 12 further comprising a plurality of object holders cooperating with the bores, each object holder having a stem receivable in the respective bore.

15. The apparatus of claim 14 further comprising a moistening tray for receiving the object holders and wetting undersides thereof with alcohol prior to placement of the object holders in the bores.

16. The apparatus of claim 15 wherein the moistening tray includes a moistening pad and a holding structure, the holding structure having two positions, a first closed position wherein the object holders are received by the moistening tray with undersides thereof contacting the moistening pad and a second open position wherein at least a portion of the object holders are in spaced relation with the moistening pad.

17. A moistening tray for holding object holders and wetting underside surfaces thereof with alcohol, the moistening tray comprising:
a) a liquid permeable moistening pad; and b) a holding structure, the holding structure having two positions, a closed position wherein object holders are received by the moistening tray with undersides thereof contacting the moistening pad and an open position wherein at least a portion of the object holders are lifted by the structure to a position spaced above the moistening pad.

18. The moistening tray of claim 17 wherein the holding structure is spring loaded.

19. The moistening tray of claim 18 wherein in the open position, object holders are manually pressable onto the moistening pad.

* * * * *